United States Patent [19]

Sakai et al.

[11] 3,948,899
[45] Apr. 6, 1976

[54] α-CYANOBENZYLPIPERAZINES AND A PROCESS FOR PRODUCING THE SAME

[75] Inventors: Katsumi Sakai, Kamiichi; Riitiro Iwaki, Tokyo; Katsuki Taoka, Komae; Hiroshi Nakajima, Toyama; Yasuo Yamada, Komae, all of Japan

[73] Assignees: Fuji Chemical Industry Co., Ltd.; Nippon Chemiphar Co., Ltd., Tokyo, both of Japan

[22] Filed: Aug. 7, 1974

[21] Appl. No.: 495,426

[30] Foreign Application Priority Data
Aug. 16, 1973 Japan.............................. 48-92096

[52] U.S. Cl............. 260/268 C; 260/268 R; 424/250
[51] Int. Cl.² ..................................... C07D 295/18
[58] Field of Search ................. 260/268 CN, 268 C

[56] References Cited
UNITED STATES PATENTS

OTHER PUBLICATIONS
Josef Klosa *Chemical Abstracts* Vol. 58, 7935(*d*), (1963).

Primary Examiner—Richard J. Gallagher
Assistant Examiner—Jose Tovar
Attorney, Agent, or Firm—Oblon, Fisher, Spivak, McClelland & Maier

[57] ABSTRACT

α-Cyanobenzylpiperazines represented by the formula

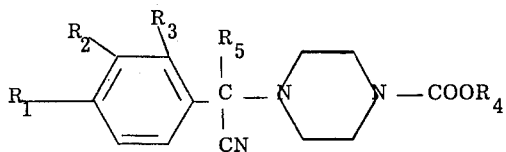

or an acid addition salt thereof, wherein $R_1$ is a halogen or 1–3C lower alkoxy, $R_2$ and $R_3$ are each hydrogen or 1–3C lower alkoxy, $R_4$ is 1–3C lower alkyl, and $R_5$ is hydrogen or 1–3C lower alkyl, which are produced by reacting an aromatic carbonyl compound with hydrogen cyanide or a salt thereof and N-alkoxycarbonyl piperazine or an acid addition salt thereof.

7 Claims, No Drawings

α-CYANOBENZYLPIPERAZINES AND A PROCESS FOR PRODUCING THE SAME

BACKGROUND OF THE INVENTION

1. Field of the Invention

This invention relates to α-cyanobenzylpiperazine and acid addition salts thereof, and also to a process for producing the same.

2. Description of the Prior Art

Recently, a number of products have been developed in response to a social demand for therapeutic and prophylactic drugs which are effective for the treatment of various circulation diseases, such as in cerebral and coronary circulation.

Particularly preferred is 2,3,4-trimethoxybenzylpiperazine dihydrochloride, which is currently marketed under the name of Vastarel F (generic name: trimetazidine dihydrochloride). This compound has been shown to be clinically effective as an antianginal drug, and the pharmacological effect has been to increase coronary blood flow and to enhance myocardial metabolism. However, the effects are relatively transitory and the drug has the disadvantage of having a depressant effect on the heart.

SUMMARY OF THE INVENTION

Accordingly, it is one object of this invention to provide novel α-cyanobenzylpiperazine compounds.

It is another object of this invention to provide α-cyanobenzylpiperazine and acid addition salts thereof which are effective in the treatment of ischemic heart disease.

It is a further object of this invention to provide a process for producing these novel compounds.

These and further objects as will become more fully apparent when consideration is given to the following detailed disclosure, have been attained by providing a compound represented by the formula (I)

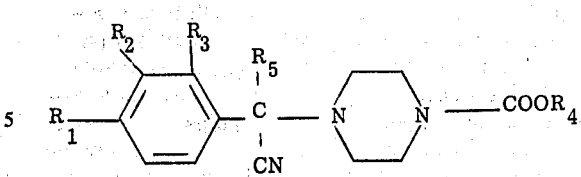

wherein $R_1$ is a halogen atom or 1–3C lower alkoxy group, $R_2$ and $R_3$ are a hydrogen atom or 1–3C lower alkoxy group, $R_4$ is 1–3C lower alkyl group, and $R_5$ is a hydrogen atom or 1–3C lower alkyl group.

DETAILED DESCRIPTION OF PREFERRED EMBODIMENTS

According to this invention, α-cyanobenzylpiperazine of the formula (I) are produced, according to the following reaction scheme, by reacting aromatic carbonyl compounds of the formula (II) with N-alkoxycarbonylpiperazines of the formula (III) and hydrogen cyanide of the formula (IV), or salts thereof.

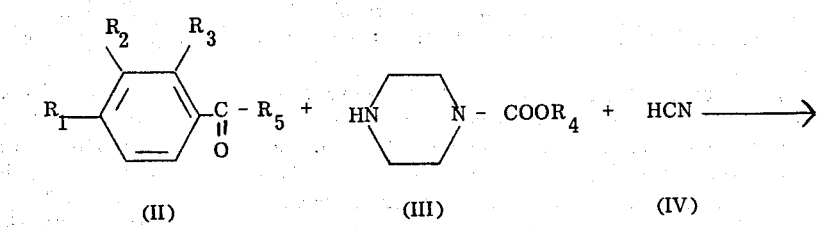

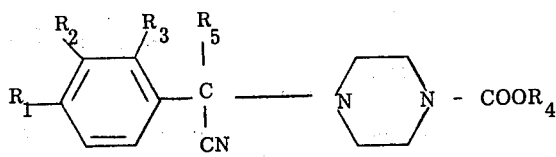

wherein $R_1$ to $R_5$ are the same as defined above.

Namely, this invention provides a process for producing novel α-cyanobenzylpiperazines through α-cyanoamination of carbonyl compounds by known methods, generally represented by the Strecker Reaction. Accordingly, a salt of hydrogen cyanide which can easily liberate hydrogen cyanide by use of an acid, can also be used in this invention. In this case, the object of this invention can be achieved by adding equal moles of an acid together with N-alkoxycarbonylpiperazine to said salts.

In practicing this invention, the three starting materials may be reacted in various forms regardless of the reaction order.

In more detail (1) at the start, aromatic carbonyl compounds are reacted with N-alkoxycarbonylpiperazine or an acid addition salt thereof, followed by the addition of hydrogen cyanide or a salt thereof or solution thereof, or alternatively (2) hydrogen cyanide or a salt thereof is first added to an aromatic carbonyl compound. In this case, acceleration of the reaction may be accomplished by the use of sodium sulfite or sodium hydrogen sulfite. Subsequently N-alkoxycarbonylpiperazine is added to the resulting mixture to yield the product in excellent yields. In view of procedural ease and availability of materials most industrially convenient processes comprise treating a salt of hydrogen cyanide. Preferable salts to be used include those such as potassium, sodium and copper cyanide which easily liberate hydrogen cyanide by the use of an acid.

In the present invention, any inert solvent may be used. Of these, particularly preferred are the polar solvents, such as methanol, ethanol, water and dimethylformamide, in view of this solubility and reactivity. Mixtures of solvents may also be employed.

The reaction will proceed sufficiently at room temperature, and as the case may be, it is necessary to cool the reactant because the reaction is exothermic. The mixture may be heated to accelerate the reaction, to yield an excellent result.

The preferred acid addition salts of N-alkoxycarbonylpiperazines to be used in the present invention include mineral acid salts thereof, such as hydrochloride and hydrobromide. When free hydrogen cyanide is directly used, the reaction can be carried out using a solution containing hydrogen cyanide, or by absorbing hydrogen cyanide in a solution containing other materials.

The pharmacological effects of N-($\alpha$-cyano-3,4-dimethoxybenzyl)-N'-ethoxycarbonyl piperazine (abbreviated hereinafter as compound B-O1) of the present invention were examined in comparison with those of Vastarel F (generic name: trimethazidine dihydrochloride) being on the market as an antianginal drug. The compounds tested had the following structural formulae.

MF-5) and $P_{o2}$ Macro electrode (Beckmann Moder 160-C), respectively, using Morawitz cannulization technique. Heart rate was measured by cardiotachometer (Nippon Koden RT-2) synchronized with systolic blood pressure of aorta.

The work done by the left ventricle is calculated according to the following equation:

The work of the left ventricle (Kg/min)=arterial mean blood pressure (mmHg) X aortic blood flow (1/min) X 13.6

1. Effects on arterial mean blood pressure (See Table 1) Both compound B-O1 and Vastarel F showed hypotensive effects, wherein the effect of the former being of longer duration and the effect of the later relatively transitory.
2. Effects on aortic blood flow (See Table 2) Vastarel F caused a marked decrease in aortic blood flow immediately after administration, followed by an increase of long duration. Compound B-O1 increased aortic blood flow by 2–8%, effect of which being of longer duration, accompanied by no decrease in blood flow immediately after medication as observed with Vastarel F.
3. Effects on coronary sinus out flow (See Table 3) Compound B-O1 exerted a marked increasing effect on coronary sinus out flow, which was proportioned to doses and of longer duration. Vastarel F caused a decrease in coronary sinus out flow in a dose of 2.0 mg/Kg due to a marked decrease in blood pressure, which was observed until after 1 minute, and then caused an increase in coronary sinus out flow only to a slight extent from 5 minutes after medication.
4. Effects on coronary sinus oxygen tension (See Table 4) Compound B-O1 caused a significant Compounds          Structural formulae compound B-O1

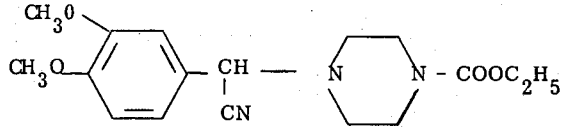

Vastarel F

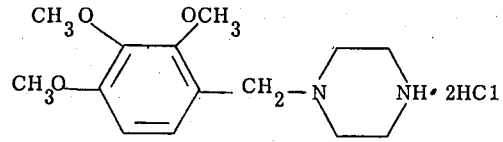

All experiments were conducted on male and female thoractomized mongrel adult dogs weighing about 10 Kg under anesthesia with pentobarbital sodium. Test compounds were suspended in 0.2% CMC solution and active placebo being dissolved in physiological saline solution. Animals were administered the drug intravenously on brachiuma with either test compound or active placebo.

Arterial blood pressure was measured by pressure transducer (Nippon Koden MPU-0.5) connected with the cannula inserted from exposed carotid artery into aorta. Aortic blood flow was determined by means of electromagnetic flow meter (Nippon Koden MF-5) mounted at an origin of aorta. Coronary sinus out flow and coronary sinus oxygen tension were assessed by means of electromagnetic flow meter (Nippon Koden increase in coronary sinus oxygen tension, effect of which was proportioned to an increase in coronary sinus out flow and of longer duration. Vastarel F caused a minimum increase in oxygen tension up to 5% between 5 and 20 minutes.

5. Effects on heart rate (See Table 5) Compound B-O1 showed a sight negative chromotropic effect. Vastarel F exerted a slight negative chlomotropic effect accompaned by an increase in heart rate immediatel after administration.
6. Effects on the work done by the left ventricle (see Table 6) Compound B-O1 caused a decrease in the work of the left ventricle, effect of which was of longer duration. Vastarel F showed a marked but transitory decreasing effect on the work of the left ventricle, and from 5 minutes after medication, an increase in the work done by the left ventricle was observed.

7. Acute Toxicity (See Table 7) Acute toxicity ($LD_{50}$; per os, mice) was measured in dd-0train male mice. Compound B-O1 presented significantly less toxicity than that of Vastarel F.

From these results, particularly from Table 3, and 4, it might be concluded that compounds of the present invention increase markedly coronary sinus out flow and coronary sinus oxygen tension, any effects of which are stronger and of longer duration than those of Vastarel F. Moreover, these compounds cause a decrease in the work done by the left ventricle as shown in Table 6, and they have less depressant effects on heart.

Acute toxicity ($LD_{50}$; per os, mice) of compound B-O1 was found to be 2200 mg/Kg, on the other hand, Vastarel F being 960 mg/Kg. Accordingly, the novel compounds of the present invention can be presumed to be safely administered to the patients with ischemic heart diseases, particularly angina pectoris, and provide sure improvements.

Table 1

| Compounds | Dose (mg/Kg) | No. of animals | Initial basal values (mmHg) | Effects on arterial mean blood pressure | | | | | | | |
|---|---|---|---|---|---|---|---|---|---|---|---|
| | | | | | Changes(%) of basal values | | | | | | |
| | | | | imm. | 1 | 5 | 10 | 15 | 20 | 25 | 30(min) |
| Compound B-01 | 2.0 | 5 | 104 | −4.0 | −1.5 | −2.6 | −4.2 | −4.5 | −3.8 | −4.0 | −4.5 |
| | 6.0 | 6 | 98 | −4.2 | −3.4 | −5.2 | −6.0 | −6.3 | −5.2 | −3.0 | −3.0 |
| | 20.0 | 5 | 124 | −14.5 | −16.9 | −16.9 | −16.0 | −17.7 | −17.0 | −17.4 | −14.9 |
| Vastarel F | 0.2 | 4 | 94 | −3.0 | −1.0 | −2.0 | −1.5 | −1.0 | 0 | 0 | 0 |
| | 0.6 | 5 | 96 | −6.0 | −2.0 | −1.5 | −1.0 | −1.0 | 0 | 0 | 0 |
| | 2.0 | 4 | 102 | −55.0 | −35.0 | −2.0 | −1.0 | 0 | −1.0 | −2.0 | −2.0 |

Table 2

| Compounds | Dose (mg/Kg) | No. of animals | Initial basal values (l/min) | Effects on aortic blood flow | | | | | | | |
|---|---|---|---|---|---|---|---|---|---|---|---|
| | | | | | Changes(%) of basal values | | | | | | |
| | | | | imm. | 1 | 5 | 10 | 15 | 20 | 25 | 30(min) |
| Compound B-01 | 2.0 | 5 | 1.2 | +0.5 | +4.3 | +3.7 | +2.3 | +2.0 | +1.0 | +1.0 | +1.0 |
| | 6.0 | 6 | 0.7 | +4.3 | +5.8 | +3.7 | +0.1 | +0.1 | −0.2 | +1.0 | +0.2 |
| | 20.0 | 5 | 0.8 | +6.1 | +7.3 | +10.2 | +8.0 | +3.6 | +3.3 | +1.6 | +1.0 |
| Vastarel F | 0.2 | 4 | 0.8 | 0 | 0 | 0 | 0 | 0 | 0 | 0 | 0 |
| | 0.6 | 5 | 0.7 | +1.5 | +0.5 | 0 | −1.0 | −1.0 | −1.0 | −1.5 | 0 |
| | 2.0 | 4 | 0.7 | −78.0 | 0 | +11.0 | +23.0 | +10.0 | +5.0 | +6.0 | +5.0 |

Table 3

| Compounds | Dose (mg/Kg) | No. of animals | Initial basal values (ml/min) | Effects on coronery sinus out flow | | | | | | | |
|---|---|---|---|---|---|---|---|---|---|---|---|
| | | | | | Changes(%) of basal values | | | | | | |
| | | | | imm. | 1 | 5 | 10 | 15 | 20 | 25 | 30(min) |
| Compound B-01 | 2.0 | 5 | 36.4 | +10.9 | +7.6 | +5.4 | +4.7 | +4.4 | +4.0 | +3.0 | +3.5 |
| | 6.0 | 6 | 38.0 | +12.0 | +16.6 | +17.0 | +18.0 | +10.9 | +8.5 | +8.0 | +8.0 |
| | 20.0 | 5 | 51.6 | +18.5 | +34.3 | +48.3 | +47.1 | +38.2 | +30.0 | +20.3 | +11.8 |
| Vastarel F | 0.2 | 4 | 30.0 | +4.0 | +1.0 | 0 | 0 | 0 | 0 | 0 | 0 |
| | 0.6 | 5 | 68.0 | +6.0 | +2.5 | +2.5 | 0 | 0 | 0 | 0 | 0 |
| | 2.0 | 4 | 68.0 | −13.0 | −3.0 | +3.0 | +9.0 | +8.0 | +4.0 | +1.0 | 0 |

Table 4

| Compounds | Dose (mg/Kg) | No. of animals | Initial basal values (mmHg) | Effects on coronary sinus oxygen tension | | | | | | | |
|---|---|---|---|---|---|---|---|---|---|---|---|
| | | | | | Changes(%) of basal values | | | | | | |
| | | | | imm. | 1 | 5 | 10 | 15 | 20 | 25 | 30(min) |
| Compound B-01 | 2.0 | 5 | 19.1 | +11.2 | +15.2 | +13.8 | +12.5 | +12.0 | +12.0 | +12.5 | +12.0 |
| | 6.0 | 6 | 12.4 | +18.0 | +27.5 | +27.0 | +3.0 | +25.5 | +19.6 | +16.2 | +13.5 |
| | 20.0 | 5 | 19.9 | +31.6 | +47.2 | +89.0 | +91.7 | +90.1 | +72.5 | +63.0 | +56.9 |
| Vastarel F | 0.2 | 4 | 18.5 | +3.0 | +1.0 | 0 | 0 | 0 | 0 | 0 | 0 |
| | 0.6 | 5 | 22.3 | +9.0 | +5.5 | +1.0 | 0 | 0 | 0 | 0 | 0 |
| | 2.0 | 4 | 22.0 | +3.0 | +1.5 | +2.0 | +5.0 | +5.0 | +3.0 | +0.5 | 0 |

Table 5

| Compounds | Dose (mg/Kg) | No. of animals | Initial basal values (beats/min) | Effects on heart rate | | | | | | | |
|---|---|---|---|---|---|---|---|---|---|---|---|
| | | | | | Changes(%) of basal values | | | | | | |
| | | | | imm. | 1 | 5 | 10 | 15 | 20 | 25 | 30(min) |
| | 2.0 | 5 | 184 | −5.2 | −4.7 | −0.6 | −0.4 | 0 | 0 | 0 | 0 |

Table 5-continued

| Compounds | Dose (mg/Kg) | No. of animals | Initial basal values (beats/min) | Effects on heart rate | | | | | | | |
|---|---|---|---|---|---|---|---|---|---|---|---|
| | | | | imm. | 1 | 5 | 10 | 15 | 20 | 25 | 30(min) |
| | | | | | Changes(%) of basal values | | | | | | |
| Compound B-01 | 6.0 | 6 | 186 | −5.0 | −3.9 | −2.3 | −0.9 | +0.6 | +1.0 | +1.0 | +1.0 |
| | 20.0 | 5 | 176 | −7.0 | +1.5 | 0 | −1.8 | −2.6 | −6.0 | −6.3 | −6.7 |
| | 0.2 | 4 | 176 | +1.5 | 0 | −1.5 | −1.0 | 0 | 0 | 0 | 0 |
| Vastarel F | 0.6 | 5 | 150 | +1.5 | +0.5 | +0.5 | 0 | −1.0 | −1.0 | −1.0 | 0 |
| | 2.0 | 4 | 150 | +5.5 | −2.0 | −2.0 | −1.5 | −1.0 | −1.5 | −1.0 | −1.5 |

Table 6

| Compounds | Dose (mg/Kg) | No. of animals | Initial basal values (Kg/min) | Effects on the work of left ventricle | | | | | | | |
|---|---|---|---|---|---|---|---|---|---|---|---|
| | | | | imm. | 1 | 5 | 10 | 15 | 20 | 25 | 30(min) |
| | | | | | Changes(%) of basal values | | | | | | |
| | 2.0 | 5 | 1.7 | −3.6 | +2.7 | +0.8 | −2.0 | −2.6 | −2.9 | −3.1 | −3.6 |
| Compound B-01 | 6.0 | 6 | 1.0 | −0.1 | +2.3 | −1.7 | −5.9 | −8.3 | −5.3 | −2.0 | −2.8 |
| | 20.0 | 5 | 1.3 | −8.5 | −10.9 | −8.4 | −9.2 | −14.8 | −14.3 | −16.1 | −14.1 |
| | 0.2 | 4 | 1.0 | −2.5 | −1.0 | −2.5 | −1.5 | −1.0 | 0 | 0 | 0 |
| Vastarel F | 0.6 | 5 | 0.9 | −4.5 | −2.0 | −1.5 | −2.0 | −2.0 | −1.0 | −1.5 | 0 |
| | 2.0 | 4 | 1.0 | −90.0 | −35.0 | +9.0 | +21.5 | +10.0 | +4.0 | +3.5 | +3.0 |

Table 7
Acute Toxicity

| Compounds | $LD_{50}$ |
|---|---|
| Compound B-01 | 2200 mg/Kg |
| Vastarel F | 960 mg/Kg |

The following Examples are given by way of illustration only and are not to be construed as limiting.

EXAMPLE 1

15.75 g. of 3,4-Dimethoxybenzaldehyde and 15.0 g. of N-ethoxycarbonylpiperazine were dissolved in 60 ml of methanol, and 9.88 g. of conc. hydrochloric acid was added thereto, and then 4.65 g. of sodium cyanide in 30 ml of water was added dropwise with stirring at room temperature over a period of 30 minutes. After addition, the resultant mixture was heated with stirring at 50°C. for 2 hours. When the mixture was heated, crystals were separated. The crystals were collected by filtration, and recrystallized from ligroin to give 30 g. of N-(α-cyano-3,4-dimethoxybenzyl)-N'ethoxycarbonylpiperazine having a melting point of 101.0° to 103.5°C.

Elemental Analysis: as $C_{17}H_{23}N_3O_4$.
Calculated (%): C, 61.25; H 6.96; N, 12.60.
Found (%): C, 61.46; H, 7.46; N, 12.64.

EXAMPLE 2

3 g. of 3,4-Dimethoxybenzaldehyde was dissolved in 15 ml of methanol, and 8 ml of aqueous solution saturated with sodium hydrogensulfite was added thereto with cooling. To the resulting mixture was added 0.95 g. of sodium cyanide in 10 ml of water, and the mixture was vigorously stirred. 3 g. of N-ethoxycarbonylpiperazine in 5 ml of methanol was added thereto and the mixture was stirred at about 50°C. for 3 hours. After the completion of reaction, solvent was evaporated, and 10 ml of water and 20 ml of benzene were added to residue. Benzene layer was collected, dired over sodium sulfate, and benzene was distilled off to give crystalline residue. Recrystallization from ligroin afforded 5 g. of crystals having a melting of 101.0° to 103.5°C. The melting point of the crystals were not depressed by admixture with N-(α-cyano-3,4-dimethoxybenzyl)-N'-ethoxycarbonylpiperazine obtained in Example 1, and the infrared absorption and N.M.R. of the crystals were identical with those of the standard sample.

EXAMPLE 3

2.48 g. of 2,3,4-Trimethoxybenzaldehyde and 25 g. of N-ethoxycarbonylpiperazine hydrochloride were dissolved in 10 ml of methanol, and 0.62 g. of sodium cyanide in 5 ml of water was added thereto, and then the mixture was stirred at 49° to 50°C. for 2 hours. After completion of the reaction, solvent was evaporated under reduced pressure, and the resultant was dissolved in 10 ml of benzene. The benzene solution was washed with water and dried over sodium sulfate, and then benzene was evaporated to give 4.3 g. of N-(α-cyano-2,3,4-trimethoxybenzyl)-N'-ethoxycarbonylpiperazine as an oily substance.

The oily substance was dissolved in benzene, and dry hydrochloric acid gas was saturated therein, and then separated crystals were collected by filtration, recrystallized from tetrahydrofuran to give N-(α-cyano-2,3,4-trimethoxybenzyl)-N'-ethoxycarbonylpiperazine hydrochloride having a melting point of 137.5° to 139.0°C.

Elemental Analysis: as $C_{18}H_{25}N_3O_5 \cdot HCl$.
Calculated (%): C, 54.07; H, 6.55; N, 10.51.
Found (%): C, 54.05; H, 6.74; N, 10.57.

EXAMPLE 4

2.48 g. of 2,3,4-Trimethoxybenzaldehyde and 2.0 g. of N-ethoxycarbonylpiperazine were dissolved in 20 ml of methanol, and ethanol solution of hydrogen cyanide prepared from 1 g. of sodium cyanide and sulfulic acid was added thereto. The mixture was reacted at a room temperature for 2 hours, and then stirred at 50°C. for 2 hours so as to complete the reaction. Thereafter, when treated in a method of the Example 3, there was obtained 4.1 g. of N-(α-cyano-2,3,4-trimethoxybenzyl)-N'-ethoxycarbonylpiperazine hydrochloride.

The melting point of the product was not depressed by admixture of standard sample obtained in Example 3, and the infrared absorption was identical with the same.

EXAMPLE 5

To the mixture of 12.8 g. of N-ethoxycarbonylpiperazine, 13 ml of water and 7.1 ml of 35% hydrochloric acid was added 10 g. of p-methoxybenzaldehyde dissolved in 40 ml of methanol over a period of 5 minutes at 5°–10°C. A solution of 3.96 g. of sodium cyanide in 10 ml of water was added to this solution over a period of about 30 minutes with stirring at the same temperature. The mixture was further stirred for 2 hours at 40°C. The solvent was distilled off to give the residure which was dissolved in benzene. This solution was washed with dilute hydrochloric acid and water, and dried over sodium sulfate. The solvent was distilled off to give 19.5 g. of N-(α-cyano-4-methoxybenzyl)-N'-ethoxycarbonylpiperazine as an oily substance. This product was dissolved in benzene and the resultant solution was saturated with dry hydrochloric gas to separate crystal which was collected by filtration. Recrystallization from acetone afforded crystals having a melting point of 170°C.

Elemental Analysis: as $C_{16}H_{21}N_3O_3 \cdot HCl$
Calculated (%): C, 56.66; H, 6.53; N, 12.37.
Found (%): C, 56.60; H, 6.86; N, 12.87.

EXAMPLE 6

The procedure of Example 5 was repeated under the same conditions, there was obtained N-(α-cyano-4-chlorobenzyl)-N'-ethoxycarbonylpiperazine hydrochloride having a melting point of 166°C. Yield 80%.

Elemental Analysis: as $C_{15}H_{18}N_3O_2Cl \cdot HCl$
Calculated (%): C, 52.34; H, 5.56; N, 12.21.
Found (%): C, 52.28; H, 5.61; N, 12.27.

EXAMPLE 7

1 g. of 3,4-Dimethoxyphenylethylketone, 1 g. of N-ethoxycarbonylpeperazine hydrochloride, 0.25 g. of sodium cyanide, 2 ml of ethanol and 6 ml of water were mixed, and the mixture was stirred at 82°C. for 6 hours. After cooling, 5 ml of water was added to the reaction mixture, and this solution was extracted with benzene. Benzene layer was reextracted with 10 % hydrochloride acid, and the extract was washed with benzene, made alkaline by adding sodium hydroxide solution with ice cooling and extracted with benzene. After drying over sodium sulfate, the extract was evaporated to give 0.32 g. of N-(α-ethyl-α-cyano-3,4-dimethoxybenzyl)-N'-ethoxycarbonylpiperazine as an oily substance.

The oil was dissolved in benzene, dry hydrochloric acid gas was saturated therein, and separated crystals were collected, washed with n-hexane to give crystals having a melting point of 107° to 112°C. Further, the crystals were recrystallized from mixture of tetrahydrofuran and methanol to give N-(α-ethyl-α-cyano-3,4-dimethoxybenzyl)-N'-ethoxycarbonylpiperazine hydrochloride having a melting point of 110° to 113°C.

Elemental Analysis: as $C_{19}H_{27}N_3O_4 \cdot HCl$.
Calculated (%): C, 57.30; H, 6.79; N, 10.56.
Found (%): C, 56.88; H, 6.43; N, 10.09.

EXAMPLE 8

The procedure of Example 7 was repeated under the same conditions, there was obtained N-(α-methyl-α-cyano-3,4-dimethoxybenzyl)-N'-ethoxycarbonylpiperazine hydrochloride. Yield 41 %.

Elemental Analysis: as $C_{18}H_{25}N_3O_4 \cdot HCl$.
Calculated (%): C, 56.27; H, 6.51; N, 10.94.
Found (%): C, 57.78; H, 6.42; N, 10.41.

Having now fully described this invention, it will be apparent to one of ordinary skill in the art that many changes and modifications can be made thereto without departing from the spirit or scope of the invention as set forth herein:

What is claimed as new and desired to be secured by Letters Patent of the United States is:

1. α-cyanobenzylpiperazine represented by the formula

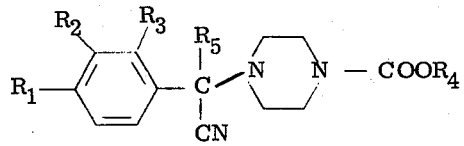

or a non-toxic acid addition salt thereof, wherein $R_1$ is halogen or alkoxy of 1–3 carbon atoms, $R_2$ and $R_3$ are each hydrogen or alkoxy of 1–3 carbon atoms, $R_4$ is alkyl of 1–3 carbon atoms, and $R_5$ is hydrogen or alkyl of 1–3 carbon atoms.

2. The α-cyanobenzylpiperazine of claim 1 which is N-(α-cyano-3,4-dimethoxybenzyl)-N'-ethoxycarbonyl-piperazine. k 3. The α-cyanobenzylpiperazine of claim 1 which is N-(α-cyano-4-methoxybenzyl)-N'-ethoxycarbonylpiperazine.

4. The α-cyanobenzylpiperazine of claim 1 which is N-(α-cyano-2,3,4-trimethoxybenzyl)-N'-ethoxycarbonylpiperazine.

5. The α-cyanobenzylpiperazine of claim 1 which is N-(α-cyano-4-chlorobenzyl)-N'-ethoxycarbonylpiperazine.

6. The α-cyanobenzylpiperazine of claim 1 which is N-(α-methyl-α-cyano-3,4-dimethoxybenzyl)-N'-ethoxycarbonylpiperazine.

7. The α-cyanobenzylpiperazine of claim 1 which is N-(α-ethyl-α-cyano-3,4-dimethoxybenzyl)-N'-ethoxycarbonylpiperazine.

* * * * *